United States Patent [19]

Kashdan

[11] Patent Number: 4,795,641
[45] Date of Patent: Jan. 3, 1989

[54] POLYMER BLENDS HAVING REVERSE PHASE MORPHOLOGY FOR CONTROLLED DELIVERY OF BIOACTIVE AGENTS

[75] Inventor: David S. Kashdan, Kingsport, Tenn. 37663

[73] Assignee: Eastman Kodak Company, Rochester, N.Y.

[21] Appl. No.: 87,566

[22] Filed: Aug. 20, 1987

[51] Int. Cl.$^4$ .......................... A61K 9/26; C08L 1/08; C09S 3/04
[52] U.S. Cl. .................................... 424/438; 106/196; 106/178; 424/488; 424/457; 514/781
[58] Field of Search ...................... 424/488, 438, 457; 514/781; 106/178, 196

[56] References Cited

U.S. PATENT DOCUMENTS

| | | | |
|---|---|---|---|
| 3,538,214 | 11/1970 | Polli et al. | 424/19 |
| 3,880,990 | 4/1975 | Bauer et al. | 424/19 |
| 3,957,523 | 5/1976 | Ohno et al. | 514/781 |
| 4,060,598 | 11/1977 | Groppenbacher et al. | 424/33 |
| 4,077,407 | 3/1978 | Theeuwes et al. | 106/196 |
| 4,177,255 | 12/1979 | Dannelly | 424/21 |
| 4,385,078 | 5/1983 | Onda et al. | 106/178 |
| 4,503,030 | 3/1985 | Edgren et al. | 424/15 |
| 4,606,771 | 8/1986 | Mukohyama et al. | 106/178 |
| 4,627,850 | 12/1986 | Deters et al. | 106/196 |
| 4,678,516 | 7/1987 | Alderman et al. | 424/488 |

OTHER PUBLICATIONS

Lee, Journal of Controlled Release, 4(1986), pp. 1-7.
(Abstract CA103(12):92855d) Ger. Offen. DE 3439722.
(Abstract CA96(6):40916s) Ger. Offen. DE 3015870.
(Abstract CA91(10):78925d) U.S. Pat. No. 4,160,020.
(Abstract CA100(12):91364u) Ger. Offen. DE 3310096.
(Abstract CA103(14):109969u) U.S. Pat. No. 4,522,625.
(Abstract CA103(22):183584f) U.K. Patent Appl. GB 2150830.
Zentner et al., J. Controlled Release, 1(1985) 269-282.
(Abstract) J. Controlled Release, 2, 217-229.
(Abstract CA83(8):62250d) U.S. Pat. No. 3,883,626.
(Abstract CA85(26):198114m) Obermayer, et al.

ACS Symp. Ser., 33 Controlled Release Polym. Formulations, Symp., (1976), 303-307.
(Abstract CA102(22):190926b) Sato, et al., Int. J. Pharm. 22(2-3), 229-255.
(Abstract CA101(2):12120f) Hou et al., Yiyao Gongye, (3), 11-18.
(Abstract CA102(22):191184v) Belgium Patent 900824.
(Abstract CA87(22):172827n) Shukla et al., Indian Drugs Pharm. Ind., 11(5), 15-16.
(Abstract CA97(22):188192u) Janicki et al., Farm. Pol., 38(6), 207-208.
(Abstract CA94(26):214548z) Bala et al., J. Macromol. Sci., Chem., A16(4), 819-827.
(Abstract CA103(14):109884n) Davidson et al., Polym. Mater. Sci. Eng., 53, 627-632.
(Abstract CA103(14):109882k) Setterstrom et al., Polym. Mater. Sci. Eng., 53, 615-619.
(Abstract CA99(2):10881w) Eur. Pat. Appl. EP 77264.
(Abstract CA102(16):133461x) Japanese Patent Appl. 83/68331.
(Abstract CA103(2):8399c) Japanese Patent Appl. 83/110047.
(Abstract) European Patent Appl. 208213.
Lee, Journal of Controlled Release, 4(1986), 1-7.
(Abstract CA100(2):12537b) Suess, Pharmazie, 38(8), 530-539.
Baker, Journal of Controlled Release, 1(1985), 321-322.

Primary Examiner—William R. Dixon, Jr.
Assistant Examiner—David M. Brunsman
Attorney, Agent, or Firm—Thomas R. Savitsky; William P. Heath, Jr.

[57] ABSTRACT

Disclosed are polymer blends containing a minor amount of cellulose acetate and a major amount of cellulose acetate phthalate, cellulose acetate trimellitate or cellulose acetate succinate. The blends have reverse phase morphology, that is, the minor component forms a continuous phase. The blends are useful for zero-order controlled delivery of bioactive agents such as pharmaceutical and agricultural chemicals.

40 Claims, 10 Drawing Sheets

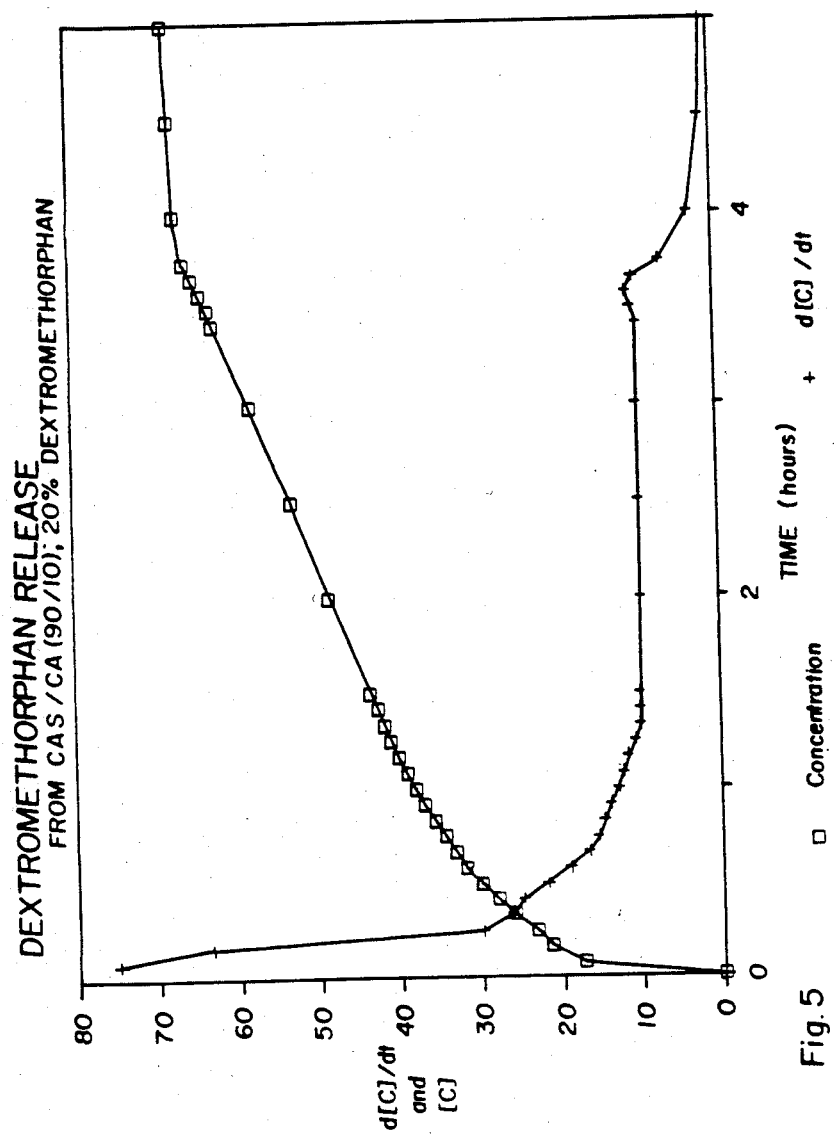

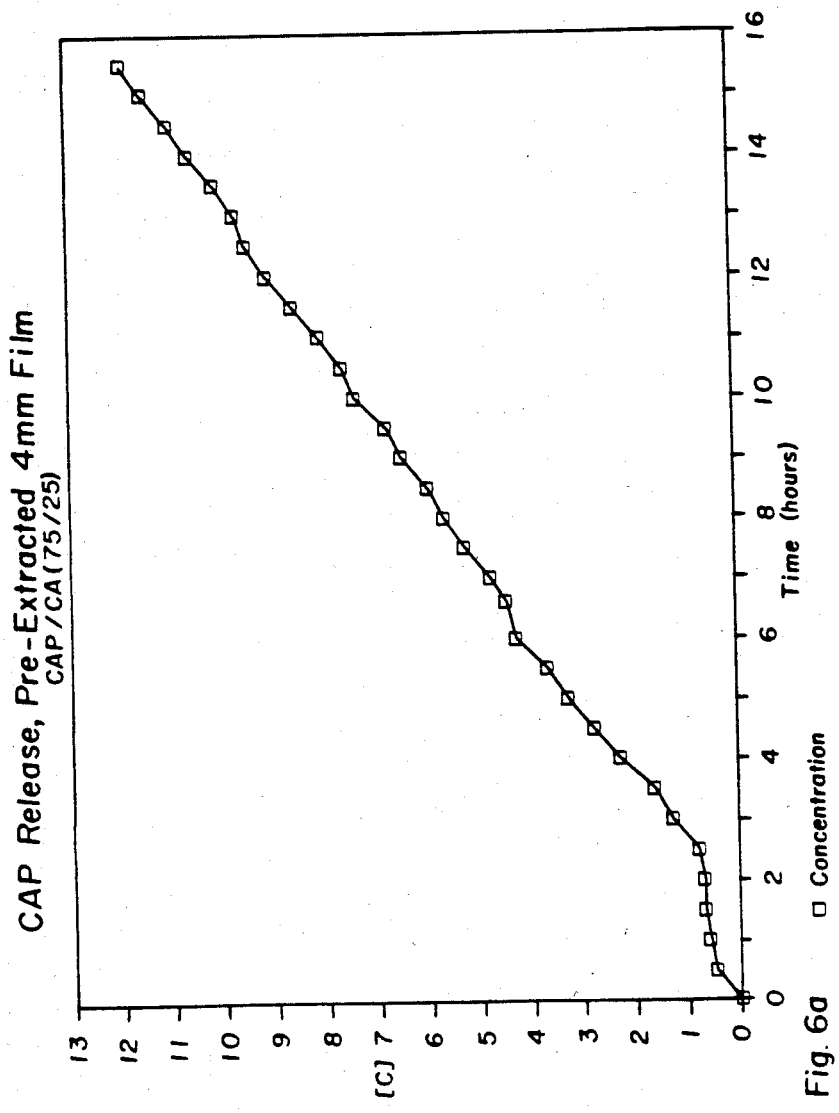

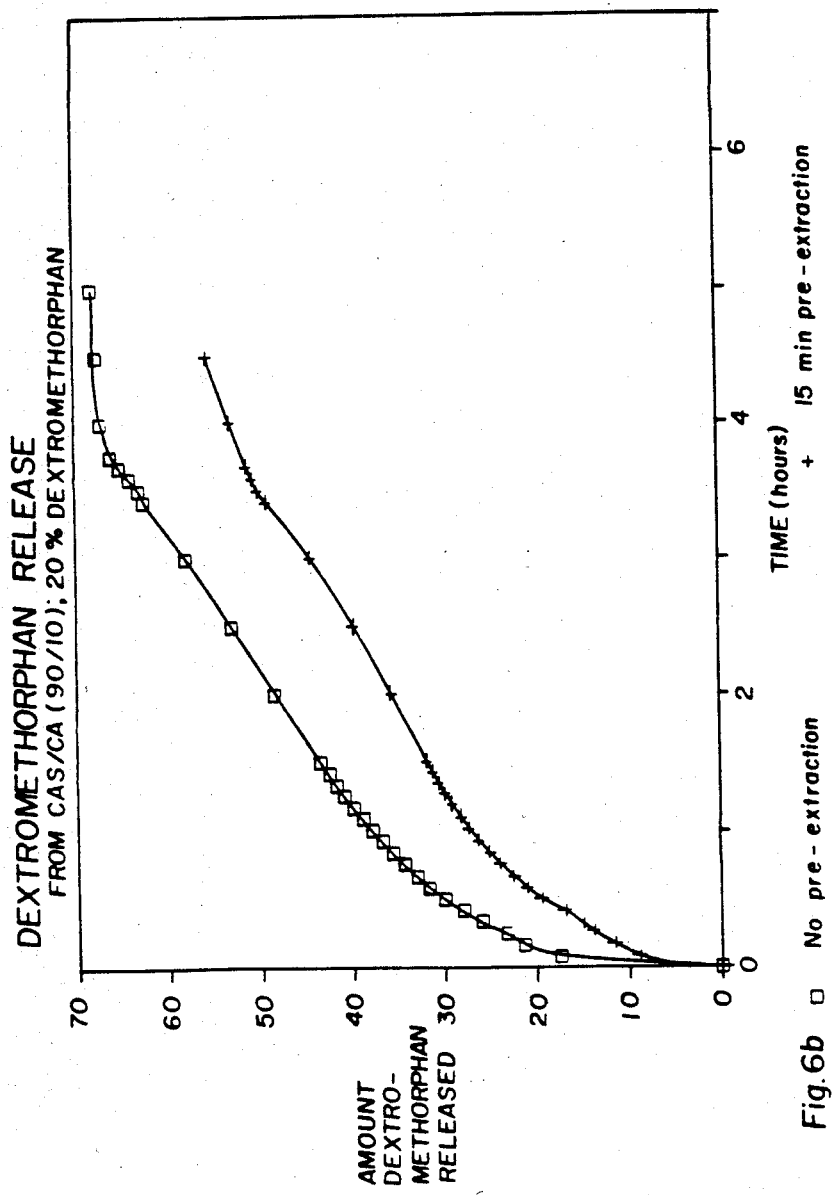

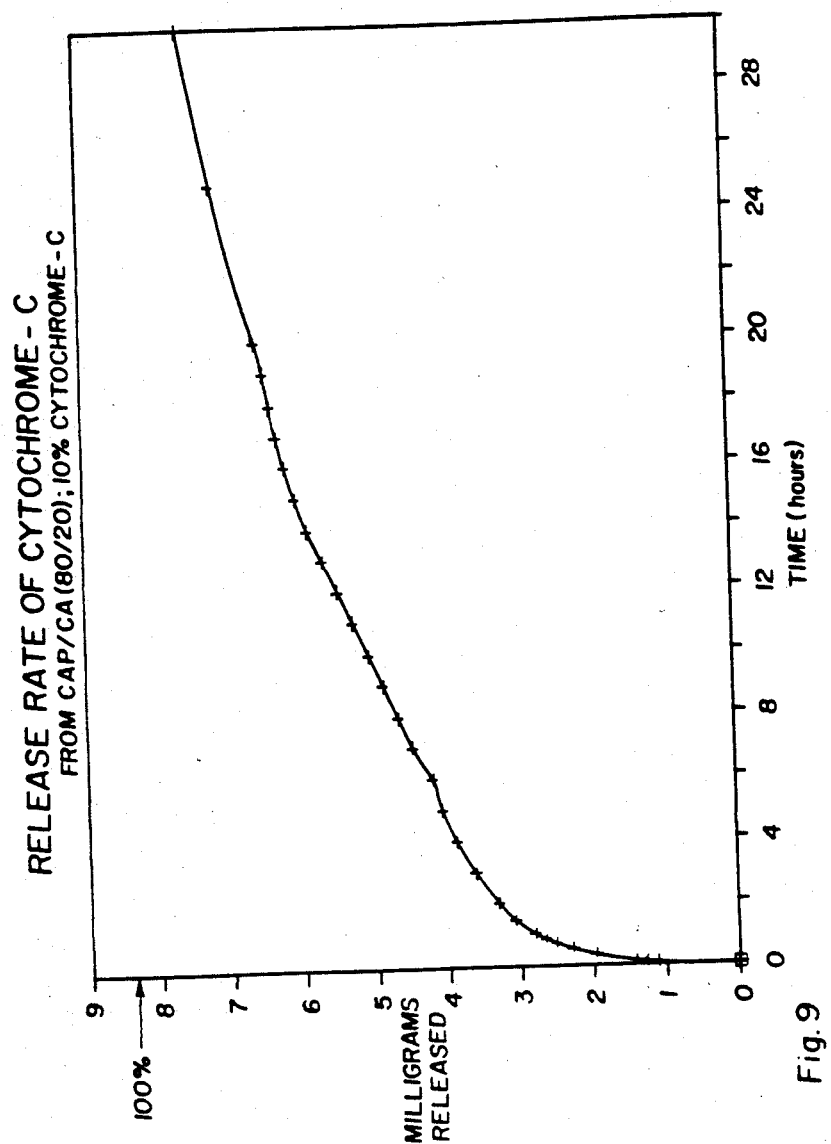

POLYMER BLENDS HAVING REVERSE PHASE MORPHOLOGY FOR CONTROLLED DELIVERY OF BIOACTIVE AGENTS

DESCRIPTION

1. Field of Invention

The present invention concerns polymer blends displaying reverse phase morphology, that is, the minor component forms a continuous phase. The blends are useful for controlled delivery of bioactive agents such as pharmaceutical and agricultural chemicals.

2. Background of the Invention

It is well known in the art that it is often desirable to deliver bioactive agents in a preprogrammed manner. Such a preprogrammed delivery is also termed controlled delivery and typically results in sustained release of the bioactive agent in vivo. There are a multitude of approaches disclosed in the prior art to achieve controlled delivery of bioactive agents. Many prior art approaches to controlled delivery involve adding a second component or carrier to the active agent, typically in the form of a coating (see, for example U.S. Pat. Nos. 4,060,598; 3,538,214; 4,177,255). The carrier acts to delay the release of the active agent in vivo. Various prior art dosage forms to achieve sustained release are based on active agent diffusion through rate limiting barriers, chemical or enzymatic degradation of a drug carrier, combinations of diffusion and degradation, and mechanical or osmotic pumping of active agent (see, for example, U.S. Pat. No. 4,503,030).

It is also known in the art that a zero-order delivery rate of the bioactive agent is desirable in many circumstances. By "zero-order" is meant that the delivery rate is independent of time during a major portion of the delivery period. Many prior art approaches for controlled delivery of active agents do not result in a zero-order delivery rate.

Substances that provide controlled delivery of bioactive agents at a zero-order release rate are highly desired.

SUMMARY OF THE INVENTION

It has been surprisingly discovered that particular blends of certain polymers exhibit reverse-phase morphology, that is, the minor polymer forms the matrix or continuous phase with the major polymer comprising discrete regions of particular dimensions within the continuous phase.

When a bioactive agent is added to such a blend, said agent is released from the blend at a zero-order rate. More specifically, the present invention is directed to a polymer blend of a soluble and insoluble polymer having reverse phase morphology wherein a soluble polymer phase comprises regions having diameters of from about 1 micrometer ($\mu$m) to the thickness of the blend dispersed in a continuous insoluble polymer phase, said polymer blend comprising (a) up to about 40 percent by weight of an insoluble polymer of cellulose acetate containing greater than about 20 percent but less than 44 percent by weight of acetyl, and (b) greater than about 60 percent by weight of a soluble polymer selected from the group consisting of cellulose acetate phthalate, cellulose acetate trimellitate, and cellulose acetate succinate.

The present invention is also directed to the polymer blend in combination with a bioactive agent wherein the polymer blend coats a bioactive agent reservoir or wherein the bioactive agent is substantially dispersed in the soluble polymer.

The present invention is also directed to a polymer matrix, optionally containing a bioactive agent, wherein the soluble polymer is extracted from the polymer blend leaving a matrix of insoluble polymer having pores of from about 1 to about 100 micrometers in diameter.

The present invention is also directed to a method for treating an animal by administering a biologically effective amount of a composition of the invention containing a bioactive agent.

As used herein "device" refers to the composition of the present invention in a form suitable for end use or administration to an animal; the term "animal" refers to any animal in which it is desired to administer a bioactive agent, including humans; "CA" refers to cellulose acetate; "CAT" refers to cellulose acetate trimellitate; "CAP" refers to cellulose acetate phthalate; and "CAS" refers to cellulose acetate succinate. Number ratios used herein which immediately follow a polymer blend description refer to the respective weight contributions of each polymer. For example, "CAS/CA (75/25)" refers to a polymer blend comprising 75 weight percent cellulose acetate succinate and 25 weight percent cellulose acetate.

BRIEF DESCRIPTION OF THE DRAWINGS

FIG. 5—Graph of the release characteristics of dextromethorphan (20%) dispersed in a CA/CAS blend. d[C]/dt is the change in concentration divided by the change in time, i.e., the rate of release. The concentration is expressed in arbitrary units.

FIG. 6a—Graph of the release characteristics of CAP from a CA/CAP blend that had been preextracted for about 10 hours. The concentration is expressed in arbitrary units.

FIG. 6b—Graph of the release characteristics of a CA/CAS blend containing 20% dextromethorphan with and without preextraction. The amount of dextromethorphan released is expressed in arbitrary units.

The amount of CAP extracted is expressed in arbitrary units.

FIG. 9—Graph of the release characteristics of a CA/CAP blend containing 10% cytochrome C.

DETAILED DESCRIPTION OF THE INVENTION

There is much known about the types of morphology which results from the mixture or blends of incompatible polymers. One class of blends are those polymers which separate into biphasic systems due to the different chemical solubility properties of different regions within each polymer molecule. Included in this category are the rubber-toughened plastics such as graft and block copolymer blends. The blends of the present invention are more similar to blends resulting from mixing two immiscible components together. Examples of this category include rubber polyblends and bicomponent and biconstituent fibers (see, for example, J. A. Mason and L. H. Spesling, *Polymer Blends and Composite*, Plenum Press, New York (1976)). The expected morphology for these blends would be the minor component existing as small spherical regions dispersed in a matrix (i.e., continuous phase) of the major component.

In such a system, if the major component is dissolved away, the minor component exists as disconnected spheres. This is in sharp contrast to the results observed in the blends of the present invention, where the minor component surrounds the surface of the spherical regions of the major component, thereby forming films of cellulose acetate surrounding the major component. This morphology is referred to herein as reverse phase morphology. If the major component is extracted out, a porous membrane of the minor component is left.

Figure 1:
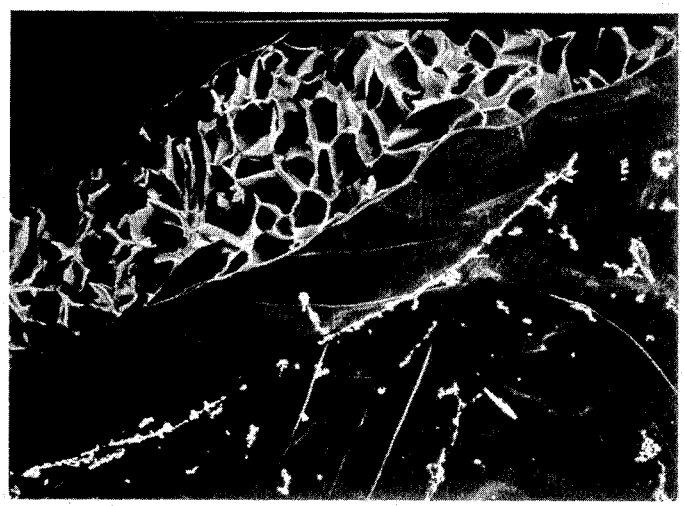
FIG. 1—photomicrograph of a polymer blend of the present invention wherein the soluble polymer had been extracted out prior to taking the photomicrograph. The empty pores represents the regions where the soluble polymer once resided. The polymer blend was composed of 25 percent by weight cellulose acetate and 75 percent by weight of cellulose acetate phthalate. The magnification is 216X.

The observed (reverse phase) morphology is illustrated in FIG. 1.

The cellulose acetate component of the blend of the present invention can be prepared by techniques known in the art. For example, cellulose acetate with various substitution levels can be made according to the method described in Kirk-Othmer, *Encyclopedia of Chemical Technology*, 3rd Edition, Vol. 5, Wiley-Interscience, NY (1979) p. 120–126. The procedure generally involves treatment of wood pulp with an excess of acetic acid and acetic anhydride in the pressence of strong acid catalyst, such as sulfuric acid. The mixture is stirred at temperatures of about 80° C. until the cellulose is completely reacted and goes into solution as the triacetate. The resulting solution is treated with aqueous base to partially neutralize the sulfuric acid, and stirred for a period of time, depending on the amount of hydrolysis desired. Typically, acetyl content of the triacetate (about 44% acetyl) is reduced to about 40%, 32% and occasionally lower values as desired. The solution is then added to water, and the precipitated polymer is filtered, washed and dried.

The cellulose acetate samples used in the Examples described herein were obtained from Eastman Chemcial Products, Inc., Kingsport, TN, and were used without modification. The commercial grades used were 394-60 (about 40% acetyl, with a viscosity of 60 seconds), 398-30 (about 40% acetyl with a viscosity rating of 30 seconds) and 320-S (about 32% acetyl). Viscosity is measured according to American Society for Testing and Materials (ASTM) ball drop procedure D871 (Formula A).

The cellulose acetate component (i.e., insoluble polymer) contains greater than about 20 percent but less than 44 percent by weight of acetyl, preferred is between about 32 and about 40 percent acetyl.

The cellulose acetate phthalate, cellulose acetate trimellitate, or cellulose acetate succinate of the blend of the present invention (i.e., soluble polymer) can be prepared by techniques known in the art. For example, cellulose acetate phthalate can be made according to the method described in U.S. Pat. No. 2,196,768. The method involves reacting Eastman cellulose acetate Type 320-S (32% acetyl) with phthalic anhydride in acetic acid with sodium acetate catalyst. The solution is allowed to react for several hours, and the polymer is precipitated by pouring the solution into water. The polymer is washed with water and dried. Analysis for % phthalyl, and % acetyl can be performed by the procedure described in the United States Pharmacopeaia/National Formulary.

The CAP samples used in the Examples herein were obtained from Eastman Chemical Products, Inc., Kingsport, TN, and were used without modification.

Cellulose acetate phthalate useful in the present invention contains between about 16 and about 24 percent by weight of acetyl and between about 20 and about 39 percent by weight of phthalyl; preferred is between about 19 and about 23 percent acetyl, and between about 32 and about 36 percent phthalyl. The samples used in the Examples herein contained about 21 percent by weight of acetyl and about 33 percent by weight of phthalyl.

Cellulose acetate trimellitate can be made according to the method described in U.S. Pat. No. 3,022,287. The method involves reacting Eastman cellulose acetate Type 320-S (32% acetyl) with trimellitic anhydride in acetic acid with sodium acetate catalyst. The solution is allowed to react for several hours, and the polymer is precipitated by pouring the solution into water. The polymer is washed with water and dried. Analysis for % trimellityl, % acetyl can be performed by the method described in the United States Pharmacopeaia/National Formulary for analyzing CAP, except that the calculations should be modified to reflect the different molecular weight of the trimellityl versus the phthalyl group.

The CAT samples used in the Example herein were obtained from Eastman Chemical Products, Inc., Kingsport, TN, and were used without modification.

Cellulose acetate trimellitate useful in the present invention contains between about 15 and about 28 percent by weight of acetyl and between about 22 and about 35 percent by weight of trimellityl; preferred is between about 18 and about 26 percent acetyl, and between about 25 and about 33 percent by weight of trimellityl. The samples used in the Examples herein contained about 23 percent by weight of acetyl and about 29 percent by weight of trimellityl.

Cellulose acetate succinate can be made according to the method described in U.S. Pat. No. 2,196,768. The method involves reacting Eastman cellulose acetate type 320-S (32% acetyl) with succinic anhydride in acetic acid with sodium acetate catalyst. The solution is allowed to react for several hours, and the polymer is precipitated by pouring the solution into water. The polymer is washed with water and dried. Analysis for % succinate and % acetyl can be performed by the method described in the United States Pharmacopeaia/National Formulary for analyzing CAP, except that the calculations should be modified to reflect the different molecular weight of the succinyl vs the phthalyl group.

Cellulose acetate succinate useful in the present invention contains between about 19 and about 29 percent by weight of acetyl, and between about 12 and about 30 percent by weight of succinyl; preferred is between about 24 and about 28 percent by weight of acetyl, and between about 14 and about 25 percent by weight of succinyl. The samples used in the Examples herein contained about 25 percent by weight of acetyl and about 22 percent by weight of succinyl.

The polymer blend of the present invention contains up to about 40 percent by weight of the insoluble polymer, preferably between about 10 and about 30 percent by weight. The blend contains greater than about 60 percent by weight of the soluble polymer, preferably between about 65 and about 90 percent by weight. However, it should be noted that specific weight ratios will vary somewhat with specific polymers in order to achieve the necessary reverse phase morphology.

The polymer blends of the present invention must exhibit reverse phase morphology. The soluble polymer phase comprises regions of from about 1 micrometer ($\mu$m) to the thickness of the blend dispersed in the continuous insoluble polymer phase; preferred are regions of between about 1 and 100 $\mu$m and most preferred are regions of between about 5 and 50 $\mu$m.

When the blends of the present invention are cast into films using standard procedures known in the polymer art, the films have three layers. That is, an upper and lower thin layer of CA (less than about 20 $\mu$m, preferably between about 1 and 10 $\mu$m) surrounds (i.e., "sandwiches") the biphasic region, i.e., blend of soluble and insoluble polymers. The two outer layers of CA are continuous with the CA in the interior of the structure. FIG. 1 illustrates the structure after the soluble polymer has been extracted from the blend.

For many applications, it is desirable to have a continuous layer of polymer (e.g., CA) completely surrounding or encapsulating the interior biphasic region in order to obtain maximum zero-order delivery. If this is not done, a large portion of the biphasic region may be directly exposed to the environment thereby resulting in a larger burst effect. In order to achieve such encapsulated compositions or dosage forms, a sheet of cast film can be cut, or punched, to obtain the desired size dosage forms. Such cut forms can then be sealed with a continuous layer of CA or other physiologically acceptable polymer by use of techniques know in the art such as solvent polishing, spray coating, immersing in polymer, and the like. Other physiologically acceptable polymers for this purpose include, for example, other cellulose esters such as cellulose acetate butyrate, cellulose acetate propionate; cellulose ethers such as methyl cellulose and ethyl cellulose; silicone based polymers; and the like. Alternatively, to achieve the desired encapsulation with CA, the compositions of the present invention can be molded, extruded, or cast into the desired shape directly, e.g., into a tablet, pill or particle. Of course, when the composition of the present invention is made by coating a bioactive agent reservoir, the polymer blend will have the desired continuous layer of CA (i.e., will be encapsulated with CA). The thickness of the encapsulating polymer will vary with the specific parameter employed, such as the type of bioactive agent, the specific delivery rate desired, and the type of polymer employed. For example, an encapsulating layer of CA will typically vary from about 1 to about 20 $\mu$m, wherein, an encapsulating layer of ethyl cellulose may be up to 100 $\mu$m due to the water swellability of ethyl cellulose.

The polymer blends of the present invention can be prepared using standard blending procedures known in the polymer art, for example, by dissolving the two polymer components in a common solvent such as 97 percent acetone/3 percent water. Other common solvents suitable for this purpose include compatible chlorinated hydrocarbon solvents such as methylene chloride, ester and ketone solvents such as methyl ethyl ketone, diethyl ketone, ethyl acetate, and the like, as well as mixtures thereof. If desired, water and lower alkyl alcohols such as methanol can be used as cosolvents. At this point it may be desirable to add a plasticizer such as triacetin, diethyl phthalate, or the like. After rolling the mixture (including, optionally, plasticizer) the resulting solution can be cast sprayed, molded, extruded, or the like.

The choice of common solvent can have distinct effects upon the release rate and delivery profile of the resulting polymer blends. The particular choice of common solvent should be made in accordance with the specific end use application desired. Films are most conveniently cast from dopes containing 20 to 25 percent solids, while sprayed films are usually made from dopes containing 5 to 10 percent solids. The film could be sprayed onto a bioactive agent core (or reservoir) or onto an inert bead (which can be used as a finished device). Other methods for preparing compositions include melt or gel extrusion. If desired, the bioactive agent can be dissolved in the polymer solution prior to casting which will result in a polymer blend with the bioactive agent intimately dispersed in the blend. After the films are cast, they are dried. After such a composition is prepared (i.e., polymer blend plus bioactive either dispersed or as a reservoir), when the composition is exposed to a solution which dissolves the soluble polymer, the bioactive agent will be released at substantially a constant rate until exhausted (zero-order). Of course, the soluble polymer is also released at substantially a zero-order rate. The polymer blends with or without bioactive agent can be cast into thin (about 50 $\mu$m) or thick (several millimeters (mm)) films.

Devices made from the composition of the present invention can also be made by molding with the use of temperature, vacuum pressure, plasticizers, or other techniques; and spinning from a melt, gel, or solution.

The shape of the device made from the compositions of the present invention is not particularly important for obtaining zero-order delivery rate of bioactive agent. While the amount of surface area affects the rate, the shape does not markedly affect the zero-order profile. This behavior is in sharp contrast to that which is expected of simple matrix delivery systems, where the shape of the dosage form device can have a strong effect on the delivery profile. This is a major advantage of the composition of the present invention in that the shapes of the compositions (or devices) can be determined by marketing considerations and ease of manufacture. As a result, the composition and/or device of the present invention can be in the shape of a tablet, bead, granule, microparticle, fiber or capsule.

The composition and/or device of this invention contain an effective amount of bioactive agent. By an "effective amount" is meant that amount present in a device or composition such that when the device or composition is administered to an animal, a desired effect results, that is, an effect that is beneficial to the animal. A typical effective amount is between about 1 and about 99 percent by weight of bioactive agent. When the bioactive agent is substantially dispersed in the soluble polymer, a preferred effective amount is between about 1 and about 35 percent by weight. When the bioactive agent is a reservoir coated by the polymer blend, an effective amount of bioactive agent is between about 85 and about 97 percent by weight.

The bioactive agents suitable for use in the composition of the present invention include human or animal drugs, dietary supplements, and agricultural chemicals. The bioactive agent may be of high molecular weight, such as insulin or bovine growth hormone, as well as low molecular weight drugs, minerals and dietary supplements.

Human and animal drugs include, but are not limited to adrenal cortical steroid inhibitors, analgesics (including aspirin, acetaminophen, ibuprofin, codeine, morphine and opium derivatives and other morphinans), anorexics (including amphetamine and non-amphetimine preparations), anti-alcohol preparations, anti-arthritics (including anti-gout preparations), anti-infective drugs (i.e., erythromycin, other anti-bacterials, anti-virals, anti-biotics such as anti-protozoals, anti-helminths, anti-anthropods, and anti-fungal agents), automatic drugs (including epinephrine, cholinergic drugs such as bethanechol and anti-cholinergic drugs such as atropine and scopolamine, adrenergic blocking drugs including alpha- and beta-blocking agents, ganglionic blocking drugs such as mecamylamine and vasodilators), anti-diabetic agents (including insulin), anti-diarheals, anti-diuretics, anti-flatulents, anti-herpes, anti-histamines (including chlorpheniramine maleate), anti-tussive agents (including dextromethorphan and codiene); respiratory drugs, including expectorants (i.e., syrup of ipecac, guaifenesin), mucolytics, decongestants (i.e., phenylephrine) and bronchodilators (i.e., ephedrine, theophylline and atropine), anti-inflammatory agents (including phenylbutazones, salicylates, steroids, 5-aminosalicyclic acid, sulfasalazene), anti-leprosy, anti-motion sickness and anti-nauseants, anti-neoplastic drugs, anti-parkinsonism drugs, anti-psychotics, anti-spasmodics and anti-cholinergics, anti-vertigo agents, cardiovascular preparations (including alpha and/or beta receptor blocking agents, anti-anginal drugs, anti-hypertensives, calcium channel blockers, digitalis, quinidine, vasodilators, and other cardiovasculars), chelating agents, cholesterol reducers, contraceptives, diuretics, dopamine receptor agonists, electrolytes (including potassium chloride) ergot preparations (including anti-migraine and uterine contractants), fertility agents, flourine preparations, hematinics (including chelated and non-chelated iron salts), histamine $H_2$ receptor antagonists (such as cimitidine and ranitidine), hormones of various types, hypnotics, immunosuppressives, laxatives (including fecal softeners, stimulates and saline types), muscle relaxants, narcotic antagonists, parasymphatholytics, parasympathomimetics, prostaglandins, quindines, CNS depressants, anti-depressants and stimulants (monoamine oxidase inhibitors, caffeine, nicotine, sedatives such as sodium amobarbital, flurazepam, etc.), thyroid preparations, trace minerals, tranquilizers (chlordiazepoxide, diazepam, lithium preparations) and X-ray contrast media, and other agents for which it may be desirable to prolong the release period and/or avoid gastric release.

Dietary supplements include, but are not limited to vitamins, minerals (such as potassium chloride), enzymes, amino acids, proteins, digestive aids and other agents taken for the purpose of increasing or maintaining health.

Agricultural chemicals include, but are not limited to, herbicides, fertilizers, growth promoters, pesticides, nematocides, fungicides and other agents which are designed to modify growth patterns of living organisms.

Another application of the polymer blends of the present invention involves extracting the soluble polymer from the blend with an appropriate solvent. Appropriate solvents are water and water containing pH buffering agents such as sodium and potassium salts, and the like. The resulting mass of porous cellulose acetate (which may or may not contain traces of soluble polymer) can then be infused with a bioactive agent which is desired to be released later at some controlled rate. The infusion can be accomplished by soaking the porous mass in a solution of the bioactive agent. The film (infused polymer matrix) will later release the bioactive agent gradually (i.e., will result in sustained or controlled release). Such release will be at a substantially zero-order rate. As with other compositions of this invention, the infused matrix can be made into any shape device. If it is desired to dry the extracted cellulose acetate device, it is especially useful to plasticize the cellulose acetate, or else the device will become brittle and shrink excessively.

Still another application of the present invention is to use the blends, after the soluble polymer has been extracted, as a membrane. Such an extracted porous film (membrane) can be used as a filtration membrane or as an osmotic membrane or as a reverse osmosis membrane for the purification of blood, water, or other fluids or gases.

The molecular weights of the polymers in the blends and compositions of the invention are not critical. However, reducing the molecular weight while keeping all other variables constant, reduces the time required for dissolution of the polymer. Typically the number average molecular weight of the cellulose acetate will vary between about 10,000 and about 120,000; whereas the molecular weight of the soluble polymer component will vary between 10,000 and 100,000.

The viscosities of the polymers in the blends of the present invention also are not particularly critical. For example, the viscosity of CA can range from about 0.05 to about 60 seconds [using ASTM D871 (Formula A)], and the viscosity of the soluble polymer can range from about 0.5 to about 60 seconds.

Subjecting the polymer solution (dope) to shear prior to its use in forming a device, causes the regions of soluble polymer to become smaller. For example, passing a cellulose acetate trimellitate/cellulose acetate dope through a 5 $\mu$m filter will cause the regions of the CAT phase to be reduced to about 5 $\mu$m in size. The smaller soluble polymer regions result in a blend in which the soluble polymer dissolves at a slower rate.

When a bioactive agent has been incorporated into a blend of the invention, some burst effect can be observed where the bioactive comes out at a higher rate for a short period of time, followed by a lower, constant rate (substantially zero-order) for a long time, until the supply of bioactive is substantially exhausted. This burst can be controlled by extracting the device for a short period (e.g., between about 5 and 60 minutes at room temperature in an appropriate solvent). If a longer period of extraction is used (e.g., between about 1 and 24 hours at room temperature in an appropriate solvent)

prior to use of the device, the resulting effect is to create an induction period during which very little bioactive agent is released. These effects can be balanced to create any combinations of release patterns desired. Pre-extraction of dosage forms as a means of modifying delivery rates is described in *J. Controlled Release*, 4, pp. 1-7 (1986), incorporated herein by reference.

Use of one or more plasticizers in the blends of the present invention will result in polymer blends that are less brittle. Suitable plasticizers are diethylphthalate, dioctylphthalate, other mono or dialkyl phthalates, glycerine, triacetin, polyethylene glycol ethers, and the like. Preferred is triacetin and diethyl phthalate. Increased amounts of water soluble plasticizers causes a more rapid release rate of the soluble polymer, while water insoluble plasticizers have more unpredictable effects on the release rate. Plasticizers can be incorporated into the polymer blends of the present invention using standard procedures known in the polymer art, for example, using a procedure substantially as described in *The Encyclopedia of Chemical Technology*, 3rd Edition, Volume 18, pp. 111-183, Wiley-Interscience, (1982).

The dissolution rate (of the soluble polymer and/or bioactive agent) of the blends of the invention will vary with pH (but still be substantially zero-order). However, within the range of physiological pH's, the soluble polymer and/or bioactive agent dissolves more rapidly as the pH is raised.

The devices of the present invention can be administered to an animal by several different means known in the art. For example, the devices can be implanted subdermally, inserted vaginally, inserted rectally, or given orally. The preferred choice of administration depends upon, among other things, the disease or condition being treated and the preference of the user.

In the method of the present invention, a biologically effective amount of the composition of the present invention containing an effective amount of bioactive agent is administered to an animal. The biologically effective amount will, of course, depend on, among other things, the effective amount of bioactive agent in the composition, the nature of the bioactive agent, the health, size, age, and species of animal, and the like. Therefore the biologically effective amount of composition to be administered can vary from nanograms to grams per kilogram of body weight per day.

The following examples are to illustrate the invention but should not be interpreted as a limitation thereon.

EXAMPLE 1

This example describes the apparatus and procedure used for measuring polymer film dissolution rate.

Figure 2:
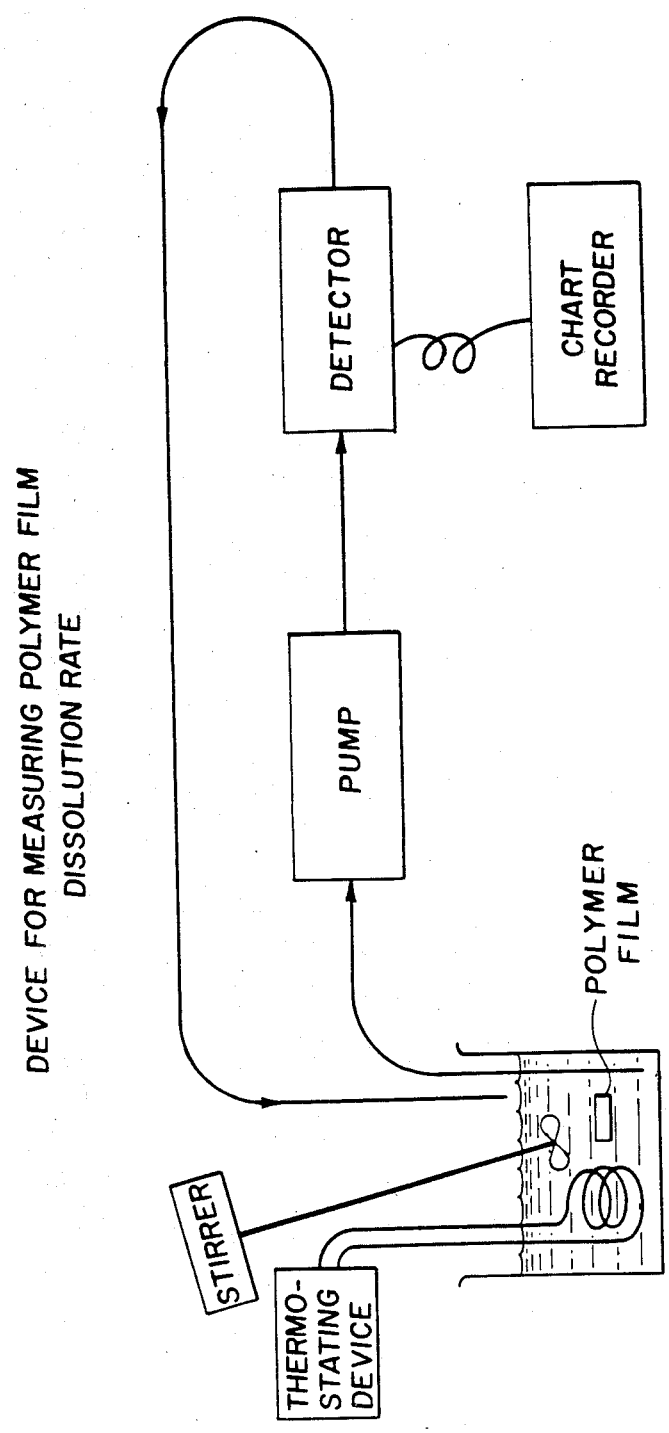
FIG. 2—Diagram of the apparatus used to measure the dissolution rate of polymers.

A diagram of the apparatus used is shown in FIG. 2. Simulated intestinal fluid is made by preparing a 0.1N solution of potassium phosphate monobasic (Mallinckrodt) and adjusting the solution to the desired pH by addition of 0.1N NaOH. It is necessary to degas the solution by subjecting it to a vacuum for approximately 3 to 4 minutes immediately prior to use, or bubbles formed in the detector making the data difficult to interpret. The reference cell of the detector is filled with a similar buffered solution. Two hundred and fifty milliliters (mL) are added to a 300-mL beaker and inserted into a constant temperature bath and allowed to equilibrate to body temperature (37° C.±0.5° C.).

A polymer film sample is prepared by casting a film on glass from a solvent (e.g., acetone) dope. After removing the film from the glass, it is allowed to dry overnight in a 54° C. oven. A sample of precisely known weight (about 20 mg if an ultraviolet (UV) detector is used, 100 mg when using a refractive index (RI) detector and precisely measured surface area, is inserted into the sample holder. The holder is then placed into the thermostated bath directly under the agitator blades with the film's surface perpendicular to the ground so that both sides of the film experience equal agitation. The agitator speed is monitored by use of a tachometer. The detector's printout gives a graph of UV absorption (or refractive index) versus time. From the detector's printout, it is possible to determine the rate of dissolution of the polymer film, measured in mg/minute/cm$^2$ (both sides of the film are considered when measuring the surface area). Generally, the rate of dissolution is linear with time. Occasionally, the first few minutes and the last few minutes exhibit a changing rate. In most cases, the first and last 10 percent of the dissolution curve are not counted for the purposes of measuring the rate.

The pump used for circulating liquids is a "Mini Pump" manufactured by the Milton-Roy Instrument Company and is operated at approximately 0.5 to 1.0 mL/minute. The UV detector is a Perkin-Elmer Model LC-15, and the RI detector is an Altex Model 156.

EXAMPLE 2

This example illustrates methods for analyzing cellulose acetate phthalate. The methods are described in the United States Pharmacopeaia/National Formulary.

Free acid—Transfer 3.0 g of CAP, previously dried, to a glass-stoppered flask, add 100 mL of dilute methanol (1 in 2) that previously has been neutralized with 0.01N sodium hydroxide to a phenolphthalein endpoint, insert the stopper in the flask, and shake for 15 minutes. Filter through paper, and wash the flask and the filter with two 10-mL portions of the neutralized methanol solution, adding the washings to the filtrate. Titrate the combined filtrate and washings with 0.1N sodium hydroxide to a phenolphthalein end-point. Each mL of 0.1N sodium hydroxide is equivalent to 8.306 mg of phthalic acid. Not more than 6.0%, calculated as phthalic acid, is found.

Acetyl-content—Transfer about 500 mg of CAP, previously dried and accurately weighed, to a conical flask, add 50 mL of water and 50.0 mL of 0.5N sodium hydroxide, insert the stopper in the flask, and allow to stand overnight. Add 5 drops of phenolphthalein solution, stir the solution at constant speed, using preferably a mechanical or a magnetic-type stirrer, and titrate with 0.5N hydrochloric acid. Add 1 mL of the acid in excess, continue the stirring for 1 hour, then titrate the excess acid with 0.5N sodium hydroxide. Perform a blank determination. Calculate the free and combined acids, as acetyl, by the formula 2.152(A/W), in which A is the volume, in mL, of 0.5N sodium hydroxide consumed after correction for the blank and W is the weight, in g, of cellulose acetate phthalate taken. Calculate the percentage of acetyl, on the acid-free basis, by the formula $[100(P-0.5182B)/(100-B)]-0.5772C$, in which P is the free and combined acids, as acetyl, B is the percentage of acid found in the test for Free acid, and C is the percentage of phthalyl found in the test for Phthalyl content.

Phthalyl content—Transfer about 1 g of CAP, previously dried and accurately weighed, to a conical flask, dissolve in 200 mL of methoxyethanol, add phenolphthalein solution, and titrate with 0.1N sodium hydroxide. Perform a blank determination, and make any necessary correction. Calculate the percentage of phthalyl, on the acid-free basis, by the formula $100[(1.491A/W)-1.795B]/(100-B)$, in which A is the volume, in mL, of 0.1N sodium hydroxide consumed after correction for the blank, W is the weight, in g, of cellulose acetate phthalate taken, and B is the percentage of acid found in the test for Free acid.

EXAMPLE 3

Various proportions of cellulose acetate of varying acetyl content and viscosity were made into blends with, respectively, cellulose acetate trimellitate, cellulose acetate phthalate, and cellulose acetate succinate. The polymers were either prepared using standard procedures known in the art or were commercial preparations available from Eastman Chemical Products, Inc., Kingsport, Tenn. The individual polymer blends were dissolved in a 97 percent acetone/3 percent water solvent and then films were cast and then dried. The presence of reverse phase morphology was checked by the dissolution test described in Example 1. The water soluble component was extracted out of the film; if the remaining CA had formed a continuous phase, the remaining polymer would consist of a swollen, porous cellulose acetate membrane. On the other hand, if the CA had not formed a continuous phase, the remaining insoluble polymer would fall apart as separate powder-like particles when the water soluble polymer was dissolved away. The results are shown in Table 1:

| Polymer Blend | Morphology |
| --- | --- |
| CA, 39.4% Acetyl, 60-Second Viscosity[1]/CAT (85/15)[3] | Reverse Phase[2] |
| CA, 39.4% Acetyl, 60-Second Viscosity/CAT (75/25) | Reverse Phase |
| CA, 39.4% Acetyl, 60-Second Viscosity/CAT (65/35) | Reverse Phase |
| CA, 39.4% Acetyl, 60-Second Viscosity/CAP (90/10) | Reverse Phase |
| CA, 39.4% Acetyl, 60-Second Viscosity/CAP (85/15) | Reverse Phase |
| CA, 39.4% Acetyl, 60-Second Viscosity/CAP (75/25) | Reverse Phase |
| CA, 39.4% Acetyl, 60-Second Viscosity/CAP (65/35) | Reverse Phase |
| CA, 39.4% Acetyl, 60-Second Viscosity/CAS (90/10) | Reverse Phase |
| CA, 39.4% Acetyl, 60-Second Viscosity/CAS (85/15) | Reverse Phase |
| CA, 39.4% Acetyl, 60-Second Viscosity/CAS (80/20) | Reverse Phase |
| CA, 39.4% Acetyl, 60-Second Viscosity/CAS (70/30) | Reverse Phase |
| CA, 39.8% Acetyl, 30-Second Viscosity/CAT (85/15) | Not Reverse Phase[4] |
| CA, 39.8% Acetyl, 30-Second Viscosity/CAT (75/25) | Reverse Phase |
| CA, 39.8% Acetyl, 30-Second Viscosity/CAT (65/35) | Reverse Phase |
| CA, 39.8% Acetyl, 30-Second Viscosity/CAT (55/45) | Not Extracted[5] |
| CA, 39.8% Acetyl, 30-Second Viscosity/CAP (85/15) | Reverse Phase |
| CA, 39.8% Acetyl, 30-Second Viscosity /CAP (75/25) | Reverse Phase |
| CA, 39.8% Acetyl, 30-Second Viscosity/CAP (65/35) | Reverse Phase |
| CA, 39.8% Acetyl, 30-Second Viscosity/CAP (55/45) | Not Reverse Phase |
| CA, 39.8% Acetyl, 30-Second Viscosity/CAS (85/15) | Not Reverse Phase |
| CA, 32% Acetyl/CAT (85/15) | Reverse Phase |
| CA, 32% Acetyl/CAP (85/15) | Not Reverse Phase |
| CA, 32% Acetyl/CAS (85/15) | Reverse Phase |

[1] Viscosity performed by ASTM D871 (Formula A).
[2] Reverse phase means that after extraction of water soluble polymer in pH 6.8 buffer, the remaining film retains its structural integrity.
[3] These numbers in parentheses represent the weight ratios of the immediately preceeding respective polymers.
[4] Not reverse phase means that when the water soluble polymer is extracted out, the remaining film disintegrates, precipitating small particles of the insoluble polymer.
[5] Not extracted means that the soluble polymer is not extracted from the film when treated with pH 6.8 buffer solution. These films retain their integrity in the buffer.

EXAMPLE 4

Figure 3:
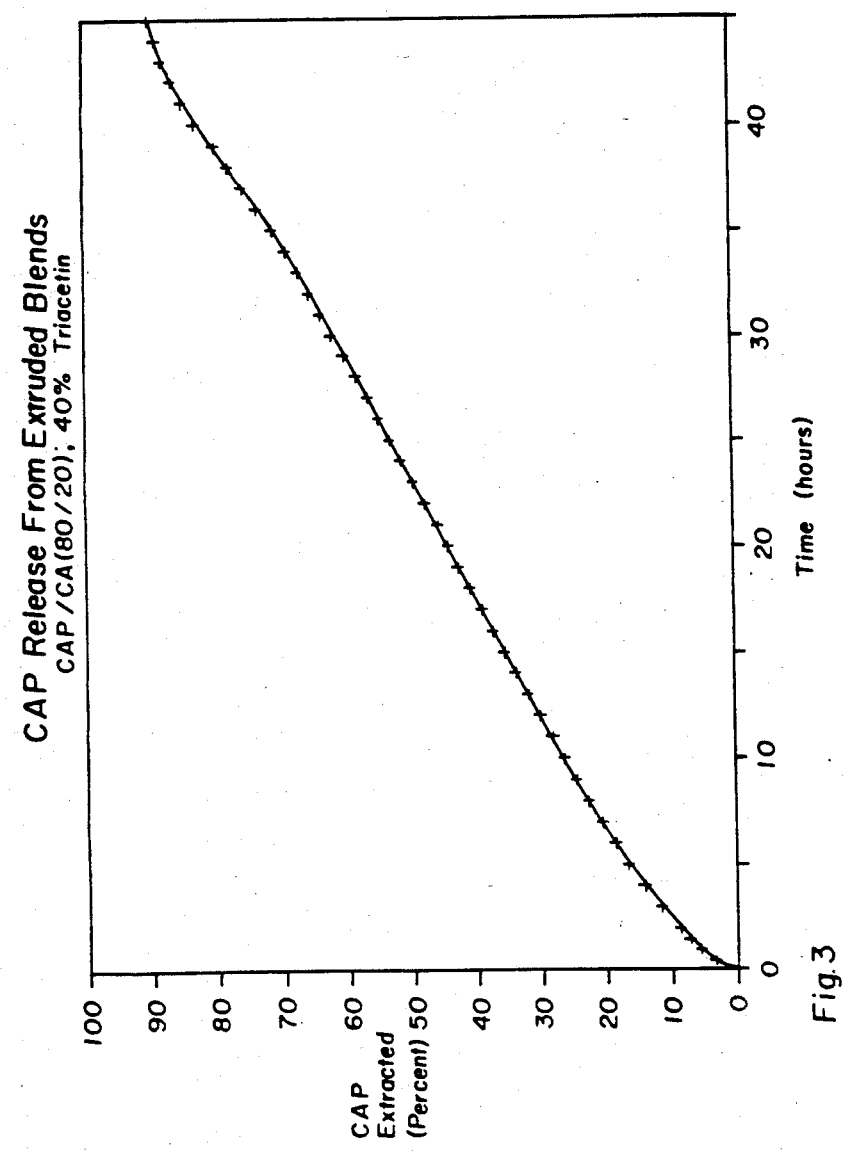
FIG. 3—Graph of the release characteristics of a blend of CA/CAP.

Pellet shaped (cylinders about 3 millimeters (mm) long × 1 mm diameter) polymer blends were prepared by melt extrusion of CAP and CA, 39.4% acetyl, 60-second viscosity (both commercially available from Eastman Chemical Products, Inc.). The plasticizer, triacetin, was also included. The finished pellets consisted essentially of 60 percent CAP/CA blend 80/20) and 40 percent triacetin. A dissolution profile of the CAP was performed using the procedure substantially as described in Example 1. The results are shown in FIG. 3 which demonstrates a zero-order release.

EXAMPLE 5

A polymer blend consisting of CAP/CA (75/25) was cast into a film of a thickness of 50 μm. The film was subjected to a dissolution analysis substantially as descried in Example 1. The soluble polymer exhibited substantially zero-order release for one to two hours.

EXAMPLE 6

A polymer blend consisting of CAP/CA (75/25) was cast into a film of a thickness of 4 mm. The film, cut into the shape of a tablet, provided over 45 hours (hrs.) of substantially zero-order delivery of the soluble polymer and the experiment was then stopped. Examination of the tablet demonstrated that the tablet was approximately one-third exhausted of the soluble polymer.

EXAMPLE 7

A series of films (polymer blends) were prepared using procedures described herein and consisted of 75 percent CAS and 25 percent CA 39.4% acetyl, 60-second viscosity ("CA-394-60").

The films were loaded with 5, 10, and 20 percent dextromethorphan (based on weight percent of polymer blend). A dissolution analysis was performed using substantially the same procedure described in Example 1. The rate of drug appearance was measured continuously by a flow through UV detector.

Figure 4:
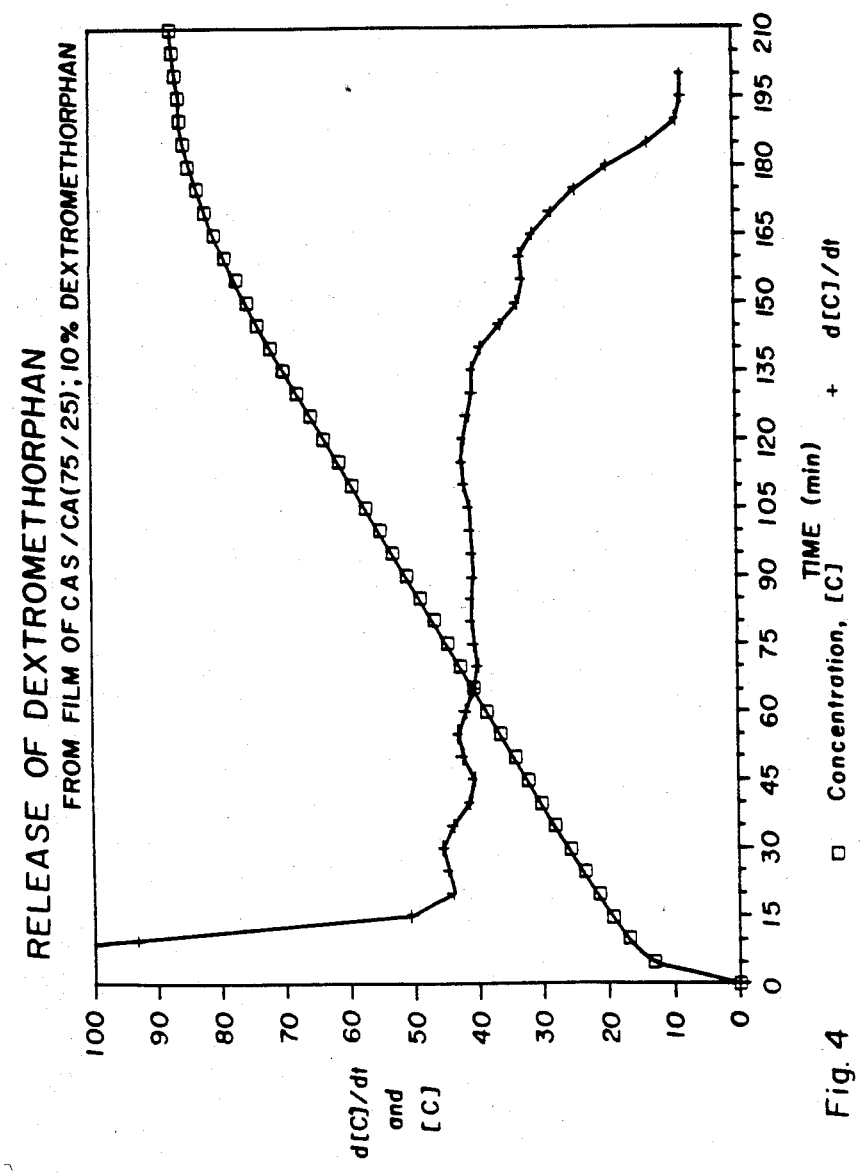
FIG. 4—Graph of the release characteristics of dextromethorphan (10%) dispersed in a CA/CAS blend. d[C]/dt is the change in concentration divided by the change in time, i.e., the rate of release. The concentration is expressed in arbitrary units.

The films containing 5 and 10 percent dextromethorphan provided essentially the same release profiles, except for the rate being doubled for the 10 percent sample. The release profile for the sample with 10 percent loading is shown in FIG. 4. About 15 percent of the drug emerged rapidly within the first 5 minutes, followed by a constant, zero-order release of the remaining drug over a period of 2.5 hours, followed by a decrease in delivery rate over the next 0.35 hours.

When the drug level was increased to 20 percent loading, the dextromethorphan crystals could not fully dissolve in the dope. Hence the resulting film contained whole crystals, in addition to the dextromethorphan which was dissolved. The needle-like crystals were about 0.5 mm long, and perhaps one-tenth of the dimension in thickness, and were clearly visible to the naked eye in the film. The release profile of this film is shown in FIG. 5. During the first 0.25 hour, about one third of the drug was released, followed by zero-order delivery for 3.5 hours. The rate then decreased to near zero over a 0.5-hour period. A thicker film would have produced a longer period of zero-order delivery.

The sample containing 20 percent dextromethorphan showed a greater "burst" effect than the sample with 10 percent loading at the beginning of its delivery profile.

EXAMPLE 8

It was observed that the release rates at the very beginning of the delivery cycle (the first 10 to 20 minutes) were often faster than the rates during the rest of the cycle ("burst").

To control the "burst" effect, a 4 mm thick film made from CAP/CA-394-60 (75/25) was used to test the concept of pre-extraction. After casting a sheet of the material, tablet-shaped pieces approximately 0.6 cm in diameter were cut out using a jig saw. These tablet-like devices were extracted in pH 6.8 buffered solution. A very significant burst effect was observed. Then the sawed edges were painted with a CA-394-60 dope to seal the region where the polymer was cut by the jig saw. This reduced the burst effect by sealing the "open" pores through which the saw had cut. The delivery device then produced a dissolution profile similar to those observed in Example 3. The tests described below were performed on these tablet-shaped device whose edges had been sealed.

During the first 0.25 hour of the dissolution profile, the delivery rate is somewhat faster than the otherwise constant rate which prevails over the following 11 hours before the extraction was halted. This device was removed from the bath, washed briefly with water and dried. When the device was re-inserted into fresh extractant, the delivery profile was recorded. As shown in FIG. 6a, the pre-extracted device now showed an induction period of almost 3 hours, followed by essentially perfect zero-order delivery for over 13 hours. These data demonstrate that an induction period can be built into a deliver device constructed of the polymer blend.

The pre-extraction process was repeated on a film of CAS/CA-394-60 containing a 20 percent loading of dextromethorphan. At this level of drug content, the dextromethorphan crystals are clearly visible in the film. The resulting curves are shown in FIG. 6b. This film showed a significant burst effect at the beginning of the extraction cycle. A large burst effect has generally been observed in systems where the drug particles are large enough to be visible to the naked eye. FIG. 6b also shows the reduced burst effect after a 15-minute pre-extraction.

EXAMPLE 9

Films of polymer blends within the scope of the invention were prepared by spreading the dope onto a glass plate. In general, the regions of soluble polymer in the resulting blends ranged from about 25 to about 100 $\mu$m in diameter.

Films of blends were also sprayed onto glass plates using commercial spray-coating equipment, the regions of soluble polymer in the blends were about 5 to 10 $\mu$m in diameter.

EXAMPLE 10

A sample of dope containing a blend within the scope of the invention was prepared and cast into a film in the usual way. A different portion of the same dope was also passed through a 5 micron filter for 2 hours, after which a film was immediately cast. A portion of the filtered dope was set aside, and samples were taken periodically and used to cast films. The freshly filtered dope had pore sizes of about 5 microns—roughly corresponding to the filter size. After less than 0.5 hour, the filtered dope had returned to its original state, and produced films indistinguishable from the film cast prior to filtering.

EXAMPLE 11

Figure 7:
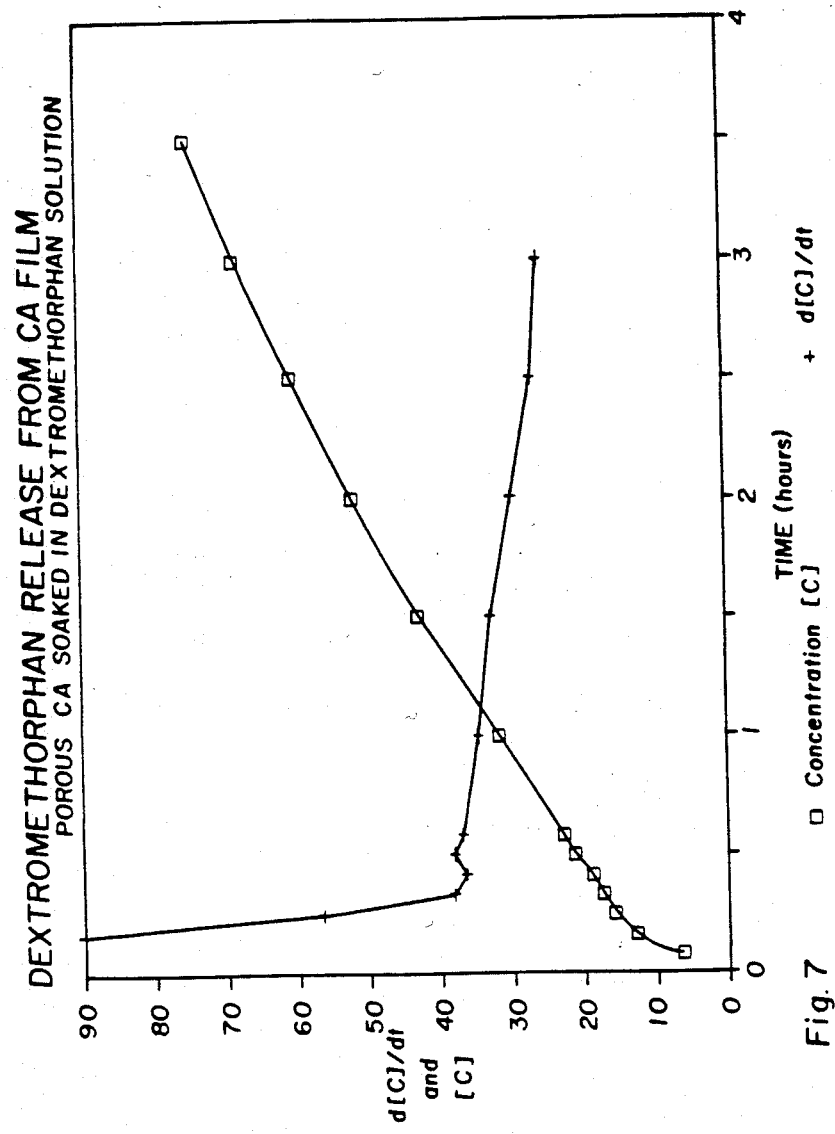
FIG. 7—Graph of the release characteristics of a CA porous film impregnated with dextromethorphan. d[C]/dt is the change in concentration divided by the change in time, i.e., the rate of release. The concentration is expressed in arbitrary units.

A porous film maded from a CA/CAP blend was prepared by extracting the CAP. The porous film of CA was then followed by soaking in a dextromethorphan solution. The wet film was then rinsed in distilled water, and the dissolution rate of the drug was mesured. The dissolution profile is shown in FIG. 7. Drying the impregnated film prior to dissolution analysis or adding glycerine to the drug solution resulted in faster dissolution profile.

EXAMPLE 12

Figure 8:
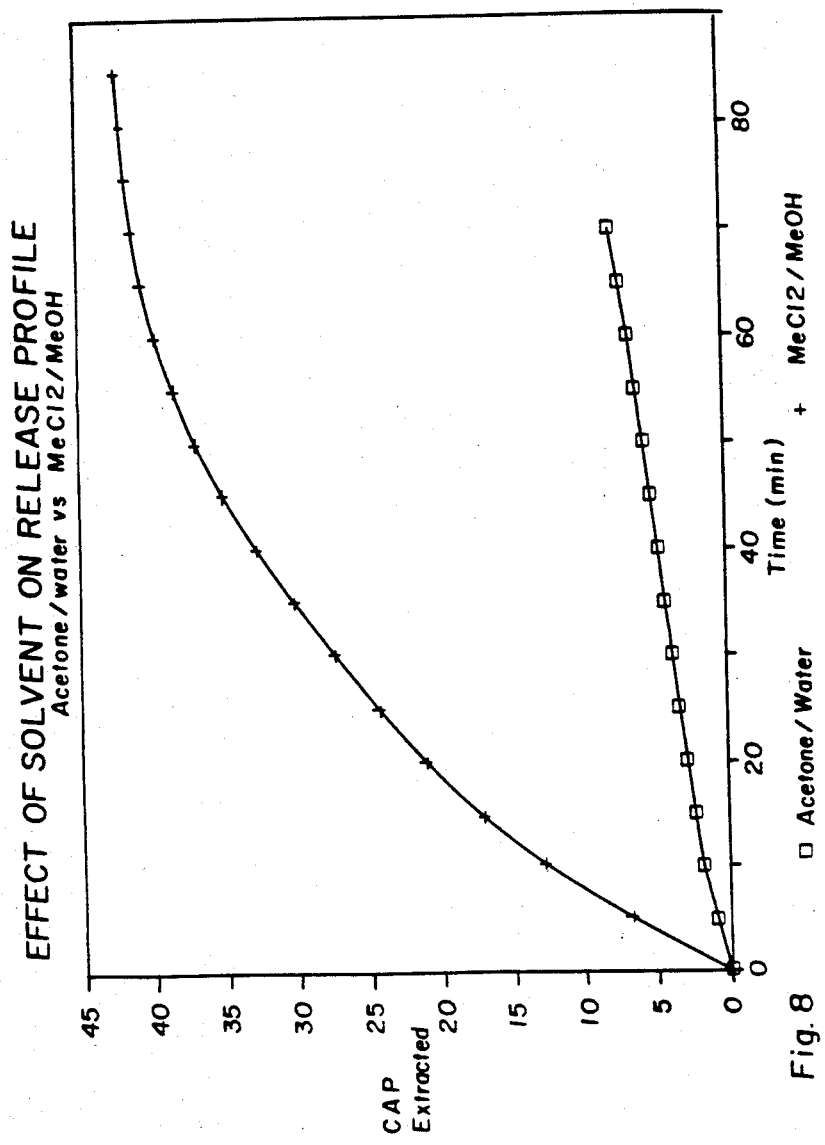
FIG. 8—Graph of release profile of CAP from a CAP/CA blend when the blends were cast from an acetone/water common solvent and from a methylene chloride (MeCl$_2$)/methanol (MeOH) common solvent.

This example illustrates the effect of the common solvent used to cast blends within the scope of the invention. CAP/CA blends were cast, respectively, from 97 percent acetone/3 percent water and 70 percent methylene chloride/30 percent methanol. The percent CAP extracted from the blends was determine using the procedure substantially as described in Example 1. FIG. 8 shows that release rates were distinctly different and that they are dependent on the solvent used for casting the device.

EXAMPLE 13

This example illustrates the use of a model protein, i.e., cytochrome C. The model protein simulates proteinaceous bioactive agents.

A blend of CAP/CA (75/25) was prepared using the procedures described herein. The blend was loaded with 10 percent cytochrome C. A dissolution analysis was performed using substantially the same procedure described in Example 1. The rate of cytochrome C appearance was measured using a UV detector. The results are shown in FIG. 9 which shows a zero-order release rate.

The invention has been described in detail with particular reference to preferred embodiments thereof, but it will be understood that variations and modifications can be effected within the spirit and scope of the invention.

I claim:

1. A polymer blend of a soluble and insoluble polymer having reverse phase morphology wherein a soluble polymer phase comprises regions dispersed in a continuous insoluble polymer phase, said polymer blend comprising
(a) up to about 40 percent by weight of an insoluble polymer of cellulose acetate containing greater than about 20 percent but less than 44 percent by weight of acetyl, and
(b) greater than about 60 percent by weight of a soluble polymer selected from the group consisting of cellulose acetate phthalate, cellulose acetate trimellitate, and cellulose acetate succinate.

2. The polymer blend of claim 1 wherein said soluble polymer phase comprises regions having diameters of from about 1 $\mu$m to the thickness of the blend.

3. The polymer blend of claim 1 wherein said soluble polymer phase comprises regions having diameters of from about 1 $\mu$m to about 100 $\mu$m.

4. The polymer blend of claim 1 wherein the amount of insoluble polymer is from about 10 to about 35 percent by weight, and the amount of soluble polymer is from about 65 to about 90 percent by weight.

5. A composition comprising a polymer blend of a soluble and insoluble polymer having reverse phase morphology wherein a soluble polymer phase comprises regions dispersed in a continuous insoluble polymer phase, said polymer blend comprising
(a) up to about 40 percent by weight of an insoluble polymer of cellulose acetate containing greater than about 20 percent but less than 44 percent by weight of acetyl, and
(b) greater than about 60 percent by weight of a soluble polymer selected from the group consisting of cellulose acetate phthalate, cellulose acetate trimellitate, and cellulose acetate succinate;
and an effective amount of a bioactive agent.

6. The composition of claim 5 wherein said effective amount is from about 1 percent to about 99 percent by weight of the total composition.

7. The composition of claim 5 wherein the bioactive agent is substantially dispersed in the soluble polymer.

8. The composition of claim 7 wherein said effective amount of bioactive agent is between about 10 and about 25 percent by weight.

9. The composition of claim 5 wherein the polymer blend coats a bioactive agent reservoir.

10. The composition of claim 9 wherein said effective amount of bioactive agent is between about 85 and 97 percent by weight.

11. The composition of claim 5 wherein the bioactive agent is a drug.

12. The composition of claim 5 wherein the bioactive agent is selected from the group consisting of adrenal cortical steroid inhibitors, analgesics, anorexics, anti-alcohol preparations, anti-arthritics, anti-infective drugs, autonomic drugs, anti-diabetic agents, anti-diarheals, anti-dimetrics, anti-flatulents, anti-herpes drugs, anti-histamines, anti-tussive agents, respiratory drugs, mucolytics, decongestants, bronchodilators, anti-inflammatory agents, anti-leprosy drugs, anti-motion sickness agents, anti-nauseants, anti-neoplastic drugs, anti-parkinsonism drugs, anti-psychotics, anti-spasmodics, anti-cholinergics, anti-vertigo agents, cardiovascular preparations, chealating agents, cholestrol reducers, contraceptives, diuretics, dopamine receptor agonists, electrolytes, ergot preparations, ferility agents, fluorine preparations, hematinics, histamine H$_2$ receptor antagonists, hormones, hypnotics, immunosuppressives, laxatives, muscle relaxants, narcotic antagonists, parasympathalytics, parasympathomimetrics, prostaglandine, quindines, central nervous system depressants, antidepressants, stimulants, thyroid preparations, trace minerals, tranquilizers, X-ray contrast media, vitamins, minerals, enzymes, amino acids, proteins, digestive aids, herbicides, fertilizers, growth promotors, pesticides, nematocides, and fungicides.

13. The composition of claim 5 wherein the bioactive agent is selected from the group consisting of aspirin, acetaminophen, ibuprofin, codeine, morphine, amphetamine, erythromycin, epinephrine, bethanechol, atropine, scopolamine, mecamylamine, insulin, chloropheniramine maleate, dextromethorphan, syrup of ipecac, quaifenesin, phenylephrine, ephedrine, theophylline, phenylbutazones, salicylates steroids, 5-aminosalicylic acid, sulfasalazene, alpha receptor blocking agents, beta receptor blocking agents, anti-anginal drugs, anti-hypertensives, calcium channel blockers, digitalis, quindine, vasodialators, potassium chloride, anti-migrane agents, uterine contractants, chelated iron salts, non-chelated iron salts, cimitidine, ranitidine, fecal softeners, fecal stimulants, monoamine oxidase inhibitors, caffeine, nicotine, sodium amobarbital, flurazepam, chlordiazepoxide, diazepam, and lithum preparations.

14. The polymer blend of claim 1 additionally containing from about 0 percent to about 40 percent by weight of a plasticizer.

15. The composition of claim 5 additionally containing from about 0 percent to about 40 percent by weight of a plasticizer.

16. The polymer blend of claim 14 wherein the plasticizer is selected from the group consisting of diethylphthalate, dioctylphthalate, other mono- or di-alkylphthalates, glycerine, triacetin, and polyethylene glycol ethers.

17. The composition of claim 15 wherein the plasticizer is selected from the group consisting of diethylphthalate, dioctylphthalate, other mono- or di-alkylphthalates, glycerine, triacetin, and polyethylene glycol ethers.

18. The polymer blend of claim 1 wherein said cellulose acetate contains between about 32 and about 40 percent by weight acetyl; said cellulose acetate phthalate contains between about 19 and about 23 percent by weight acetyl and between about 32 and about 36 percent by weight phthalyl; said cellulose acetate trimetllitate contains between about 18 and about 26 percent by weight acetyl and between about 25 and about 33 percent by weight of trimellityl; and said cellulose acetate succinate contains between about 24 and about 28 percent by weight of acetyl and between about 14 and about 25 percent by weight of succinyl.

19. The composition of claim 5 that is formed into a device in the shape of a tablet, bead, granule, microparticle, fiber, or capsule.

20. The composition of claim 5 wherein the bioactive agent is pre-extracted for a time sufficient to reduce the burst effect and leave the zero-order release characteristics substantially unaffected.

21. A polymer matrix wherein a soluble polymer is extracted from a polymer blend of a soluble and insoluble polymer having reverse phase morphology wherein a soluble polymer phase comprises regions dispersed in a continuous insoluble polymer phase, leaving a matrix of insoluble polymer having pores of from about 1 to about 100 micrometers in diameter, said polymer blend comprising
(a) up to about 40 percent by weight of an insoluble polymer of cellulose acetate containing greater than about 20 percent but less than 44 percent by weight of acetyl, and
(b) greater than about 60 percent by weight of a soluble polymer selected from the group consisting of cellulose acetate phthalate, cellulose acetate trimellitate, and cellulose acetate succinate.

22. The polymer matrix of claim 21 wherein said matrix is infused with a bioactive agent.

23. The polymer matrix of claim 22 wherein said bioactive agent is selected from the group consisting of adrenal cortical steroid inhibitors, analgesics, anorexics, anti-alcohol preparations, anti-arthritics, anti-infective drugs, autonomic drugs, anti-diabetic agents, anti-diarheals, anti-dimetrics, anti-flatulents, anti-herpes drugs, anti-histamines, anti-tussive agents, respiratory drugs, mucolytics, decongestants, bronchodilators, anti-inflammatory agents, anti-leprosy drugs, anti-motion sickness agents, anti-nauseants, anti-neoplastic drugs, anti-parkinsonism drugs, anti-psychotics, anti-spasmodics, anti-cholinergics, anti-vertigo agents, cardiovascular preparations, chealating agents, cholesterol reducers, contraceptives, diuretics, dopamine receptor agonists, electrolytes, ergot preparations, fertility agents, fluorine preparations, hematinics, histamine H2 receptor antagonists, hormones, hypnotics, immunosuppressives, laxatives, muscle relaxants, narcotic antagonists, parasympathalytics, parasympathomimetrics, prostaglandine, quinidines, central nervous system depressants, anti-depressants, stimulants, thyroid preparations, trace minerals, tranquilizers, X-ray contrast media, vitamins, minerals, enzymes, amino acids, proteins, digestive aids, herbicides, fertilizers, growth promotors, pesticides, nematocides, and fungicides.

24. The polymer matrix of claim 22 wherein said bioactive agent is selected from the group consisting of aspirin, acetaminophen, ibuprofin, codeine, morphine, amphetamine, erythromycin, epinephrine, bethanechol, atropine, scopolamine, mecamylamine, insulin, chloropheniramine maleate, dextromethorphan, syrup of ipecac, quaifenesin, phenylephrine, ephedrine, theophylline, phenylbutazones, salicylates steroids, 5-aminosalicylic acid, sulfasalazene, alpha receptor blocking agents, beta receptor blocking agents, anti-anginal drugs, anti-hypertensive, calcium channel blockers, digitalis, quinidine, vasodialators, potassium chloride, anti-migrane agents, uterine contractants, chelated iron salts, non-chelated iron salts, cimitidine, ranitidine, fecal softeners, fecal stimulants, monoamine oxidase inhibitors, caffeine, nicotine, sodium amobarbital, flurazepam, chlordiazepoxide, diazepam, and lithium preparations.

25. A method for treating an animal in need of such treatment comprising administering to said animal a biologically effective amount of a composition comprising an effective amount of a bioactive agent in combination with a polymer blend of a soluble and insoluble polymer having reverse phase morphology wherein a soluble polymer phase comprises regions dispersed in a continuous insoluble polymer phase, said polymer blend comprising
(a) up to about 40 percent by weight of an insoluble polymer of cellulose acetate containing greater than about 20 percent but less than 44 percent by weight of acetyl, and
(b) greater than about 60 percent by weight of a soluble polymer selected from the group consisting of cellulose acetate phthalate, cellulose acetate trimellitate, cellulose acetate succinate.

26. The method of claim 25 wherein the amount of insoluble polymer is from about 10 to about 35 percent by weight, and the amount of soluble polymer is from about 65 to about 90 percent by weight.

27. The method of claim 25 wherein the bioactive agent of said composition is substantially dispersed in the soluble polymer.

28. The method of claim 27 wherein the effective amount of bioactive agent in said composition is between about 10 and about 35 percent by weight.

29. The method of claim 25 wherein the polymer blend of said composition coats a bioactive agent reservoir.

30. The method of claim 29 wherein the effective amount of said composition is between about 85 and 97 percent by weight.

31. The method of claim 25 wherein the bioactive agent of said composition is a drug.

32. The method of claim 25 wherein the bioactive agent of said composition is selected from the group consisting of adrenal cortical steroid inhibitors, analgesics, anorexics, anti-alcohol preparations, anti-arthirtics, anti-infective drugs, autonomic drugs, anti-diabetic agents, anti-diarheals, anti-dimetrics, anti-flatulents, anti-herpes drugs, anti-histamines, anti-tussive agents, respiratory drugs, mucolytics, decongestants, bronchodilators, anti-inflammatory agents, anti-leprosy drugs, anti-motion sickness agents, anti-nauseants, anti-neoplastic drugs, anti-parkinsonism drugs, anti-psychotics, anti-spasmodics, anti-cholinergics, anti-vertigo agents, cardiovascular preparations, chealating agents, cholesterol reducers, contraceptives, diuretics, dopamine receptor agonists, electrolytes, ergot preparations, ferility agents, fluorine preparations, hematinics, histamine $H_2$ receptor antagonists, hormones, hypnotics, immunosuppressives, laxatives, muscle relaxants, narcotic antagonists, parasympathalytics, parasympathomimetrics, prostaglandine, quinidines, central nervous system depressants, anti-depressants, stimulants, thyroid preparations, trace minerals, tranquilizers, X-ray contrast media, vitamins, minerals, enzymes, amino acids, proteins, digestive aids, herbicides, fertilizers, growth promotors, pesticides, nematocides, and fungicides.

33. The method of claim 25 wherein the bioactive agent of said composition is selected from the group consisting of aspirin, acetaminophen, ibuprofin, codeine, morphine, amphetamine, erythromycin, epinephrine, bethanechol, atropine, scopolamine, mecamylamine, insulin, chloropheniramine maleate, dextromethorphan, syrup of ipecac, quaifenesin, phenylephrine, ephedrine, theophylline, phenylbutazones, salicylates steroids, 5-aminosalicylic acid sulfasalazene, alpha receptor blocking agents, beta receptor blocking agents, anti-anginal drugs, anti-hypertensives, calcium channel blockers, digitalis, quinidine, vasodialators, potassium chloride, anti-migrane agents, uterine contractants, chelated iron salts, non-chelated iron salts, cimitidine, ranitidine, fecal softeners, fecal stimulants, monoamine oxidase inhibitors, caffeine, nicotine, sodium amobarbital, flurazepam, chlordiazepoxide, diazepam, and lithum preparations.

34. The method of claim 25 wherein said composition additionally contains from about 0 percent to about 40 percent by weight of a plasticizer.

35. The method of claim 34 wherein said plasticizer is selected from the group consisting of diethylphthalate, dioctylphthalate, other mono- or di-alkylphthalates, glycerine, triacetin, and polyethylene glycol ethers.

36. The method of claim 25 wherein said composition is formed into a device in the shape of a tablet, bead, granule, microparticle, fiber, or capsule.

37. The method of claim 25 wherein the bioactive agent of said composition is pre-extracted for a time sufficient to reduce the burst effect and leave the zero order release characteristics substantially unaffected.

38. A method for treating an animal in need of such treatment comprising administering to said animal a biologically effective amount of a composition comprising a polymer matrix wherein a soluble polymer is extracted from a polymer blend of a soluble and insoluble polymer having reverse phase morphology wherein a soluble polymer phase comprises regions dispersed in a continuous insoluble polymer phase, leaving a matrix of insoluble polymer having pores of from about 1 to about 100 micrometers in diameter, said polymer blend comprising
(a) up to about 40 percent by weight of an insoluble polymer of cellulose acetate containing greater than about 20 percent but less than 44 percent by weight of acetyl, and
(b) greater than about 60 percent by weight of a soluble polymer selected from the group consisting of cellulose actetate phthalate, cellulose acetate trimellitate, and cellulose acetate succinate, wherein said matrix is infused with an effective amount of a bioactive agent.

39. The method of claim 38 wherein the bioactive agent of said polymer matrix is selected from the group consisting of adrenal cortical steroid inhibitors, analgesics, anorexics, anti-alcohol preparations, anti-arthritics, anti-infective drugs, autonomic drugs, anti-diabetic agents, anti-diarheals, anti-dimetrics, anti-flatulents, anti-herpes drugs, anti-histamines, anti-tussive agents, respiratory drugs, mucolytics, decongestants, bronchodilators, anti-inflammatory agents, anti-leprosy drugs, anti-motion sickness agents, anti-nauseants, anti-neoplastic drugs, anti-parkinsonism drugs, anti-psychotics, anti-spasmodics, anti-cholinergics, anti-vertigo agents, cardiovascular preparations, chealating agents, cholesterol reducers, contraceptives, diuretics, dopamine receptor agonists, electrolytes, ergot preparations, fertility agents, fluorine preparations, hematinics, histamine $H_2$ receptor antagonists, hormones, hypnotics, immunosuppressives, laxatives, muscle relaxants, narcotic antagonists, parasympathalytics, parasympathomimetrics, prostaglandine, quinidines, central nervous system depressants, anti-depressants, stimulants, thyroid preparations, trace minerals, tranquilizers, X-ray contrast media, vitamins, minerals, enzymes, amino acids, proteins, digestive aids, herbicides, fertilizers, growth promotors, pesticides, nematocides, and fungicides.

40. The method of claim 38 wherein the bioactive agent of said polymer matrix is selected from the group consisting of aspirin, acetaminophen, ibuprofin, codeine, morphine, amphetamine, erythromycin, epinephrine, bethanechol, atropine, scopolamine, mecamylamine, insulin, chloropheniramine maleate, dextromethorphan, syrup of ipecac, quaifenesin, phenylephrine, ephedrine, theophylline, phenylbutazones, salicylates steroids, 5-aminosalicylic acid, sulfasalazene, alpha receptor blocking agents, beta receptor blocking agents, anti-anginal drugs, anti-hypertensive, calcium channel blockers, digitalis, quinidine, vasodialators, potassium chloride, anti-migrane agents, uterine contractants, chelated iron salts, non-chelated iron salts, cimitidine, ranitidine, fecal softeners, fecal stimulants, monoamine oxidase inhibitors, caffeine, nicotine, sodium amobarbital, flurazepam, chlordiazepoxide, diazepam, and lithum preparations.

* * * * *

UNITED STATES PATENT AND TRADEMARK OFFICE
CERTIFICATE OF CORRECTION

PATENT NO. : 4,795,641

DATED : January 3, 1989

INVENTOR(S) : David S. Kashdan

It is certified that error appears in the above-identified patent and that said Letters Patent is hereby corrected as shown below:

Claim 8, line 2, "10 percent" should read -- 1 percent --.

Claim 8, line 3, "25 percent" should read --- 35 percent ---.

Claim 13, line 12, "quindine" should read --- quinidine ---.

Signed and Sealed this

Eighteenth Day of July, 1989

Attest:

DONALD J. QUIGG

Attesting Officer

Commissioner of Patents and Trademarks